(12) United States Patent  
Yoneyama et al.

(10) Patent No.: US 7,706,597 B2  
(45) Date of Patent: Apr. 27, 2010

(54) DEFECT INSPECTION APPARATUS AND DEFECT INSPECTION METHOD

(75) Inventors: Takashi Yoneyama, Sagamihara (JP); Eriko Tsuji, Machida (JP)

(73) Assignee: Olympus Corporation, Tokyo (JP)

( * ) Notice: Subject to any disclaimer, the term of this patent is extended or adjusted under 35 U.S.C. 154(b) by 897 days.

(21) Appl. No.: 10/773,524

(22) Filed: Feb. 6, 2004

(65) Prior Publication Data

US 2005/0175233 A1    Aug. 11, 2005

(51) Int. Cl.  
*G06K 9/00* (2006.01)

(52) U.S. Cl. ............ 382/145; 348/125; 382/144; 382/151; 382/141; 355/53; 396/90; 359/368

(58) Field of Classification Search ........... 382/145, 382/141, 144; 348/125, 134; 702/35  
See application file for complete search history.

(56) References Cited

U.S. PATENT DOCUMENTS

| | | | | |
|---|---|---|---|---|
| 4,393,309 A | * | 7/1983 | Norioka | 250/396 R |
| 4,496,971 A | * | 1/1985 | West et al. | 348/125 |
| 4,521,807 A | * | 6/1985 | Werson | 348/134 |
| 4,532,650 A | * | 7/1985 | Wihl et al. | 382/144 |
| 4,547,895 A | * | 10/1985 | Mita et al. | 382/144 |
| 4,553,834 A | * | 11/1985 | Ayata et al. | 355/53 |
| 4,841,323 A | * | 6/1989 | Yamada et al. | 396/90 |
| 4,860,374 A | * | 8/1989 | Murakami et al. | 382/151 |
| 5,710,662 A | * | 1/1998 | Nishida | 359/368 |
| 5,761,336 A | * | 6/1998 | Xu et al. | 382/141 |
| 5,801,965 A | * | 9/1998 | Takagi et al. | 702/35 |
| 6,047,083 A | * | 4/2000 | Mizuno | 382/141 |
| 6,937,754 B1 | * | 8/2005 | Eguchi | 382/145 |

FOREIGN PATENT DOCUMENTS

| | | | |
|---|---|---|---|
| JP | 61005317 A | * | 1/1986 |
| JP | 04-105049 A | | 4/1992 |
| JP | 6-165019 A | | 6/1994 |
| JP | 09-297258 A | | 11/1997 |
| JP | 11-84228 A | | 3/1999 |
| JP | 2001-189358 A | | 7/2001 |

* cited by examiner

*Primary Examiner*—Samir A. Ahmed  
*Assistant Examiner*—Tsung-Yin Tsai  
(74) *Attorney, Agent, or Firm*—Frishauf, Holtz, Goodman & Chick, P.C.

(57) ABSTRACT

A defect inspection apparatus which includes a pattern image obtaining unit obtaining a pattern image of a predetermined part by causing focusing control to be performed in order to achieve focus on the predetermined part within an observation object according to set focusing control parameters, a pattern image storing unit storing the pattern image, and a detecting unit detecting the presence/absence of an abnormal condition of a part to be inspected by making a comparison between the pattern image of a reference part within the observation object, and the pattern image of the part to be inspected within the observation object. The focusing control parameters, set when the pattern image of the part to be inspected is obtained, are determined based on sample information obtained when the pattern image of the reference part is obtained.

14 Claims, 9 Drawing Sheets

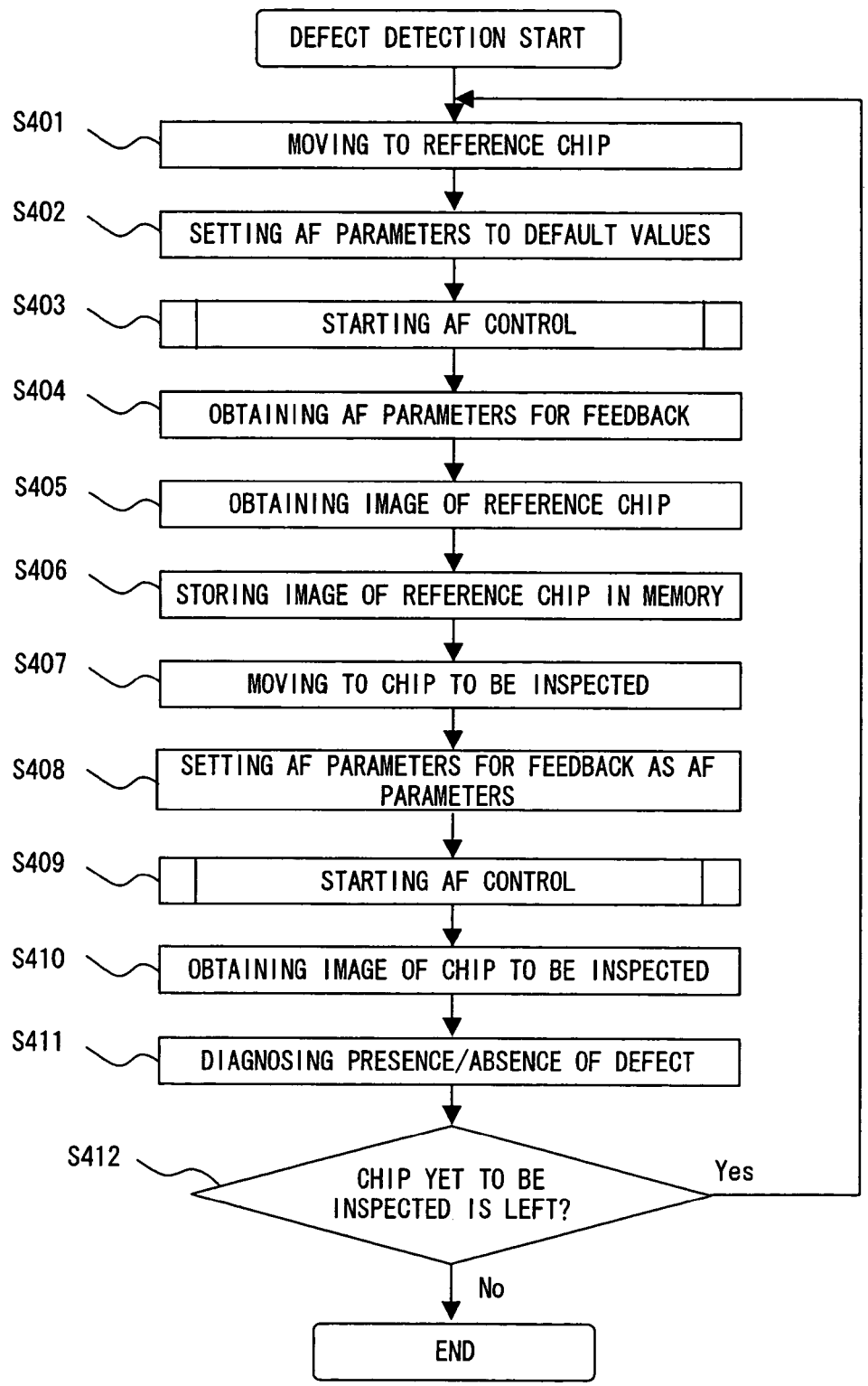
F I G. 4

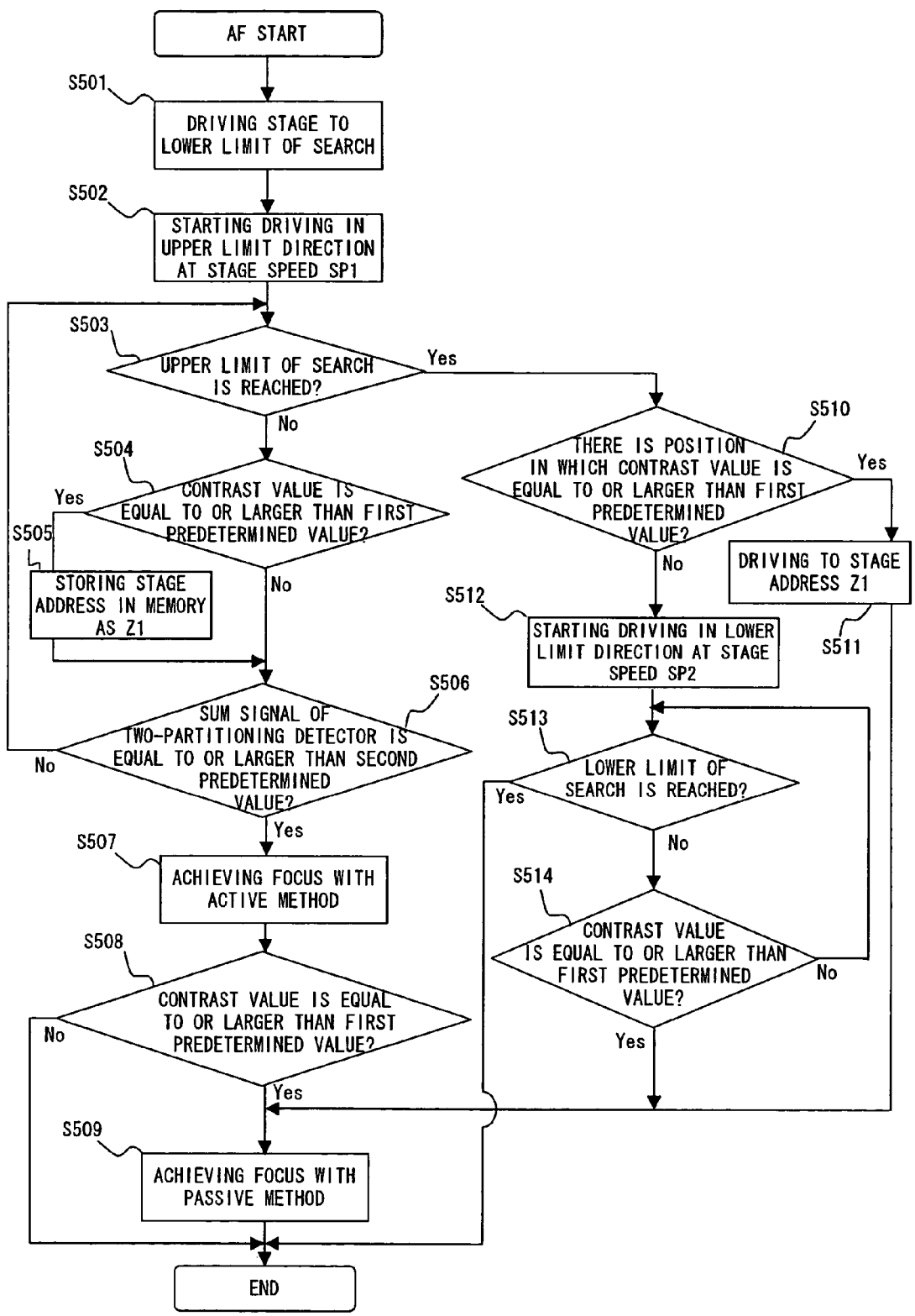
F I G. 5

| | PARAMETER | CONTENTS | EFFECT |
|---|---|---|---|
| 1 | ACTIVE AF STAGE SPEED | STAGE SPEED WHEN SAMPLE IS SEARCHED WITH ACTIVE AF | IMPROVES FOCUSING SPEED |
| 2 | SEARCH RANGE | SEARCH RANGE OF SAMPLE IN Z DIRECTION OF STAGE | IMPROVES FOCUSING SPEED |
| 3 | SAMPLE SEARCH AF METHOD | AF METHOD WHEN SAMPLE IS SEARCHED | IMPROVES FOCUSING SPEED |
| 4 | PASSIVE AF STAGE SPEED | STAGE SPEED WHEN SAMPLE IS SEARCHED WITH PASSIVE AF | IMPROVES FOCUSING SPEED |
| 5 | ACTIVE AF OFFSET AMOUNT | AF OFFSET AMOUNT AT TIME OF ACTIVE AF | IMPROVES FOCUSING ACCURACY |
| 6 | PASSIVE AF CONTRAST THRESHOLD VALUE | CONTRAST THRESHOLD VALUE WITH WHICH PRESENCE/ABSENCE OF CONTRAST IS DETECTED | IMPROVES FOCUSING ACCURACY |

F I G. 6

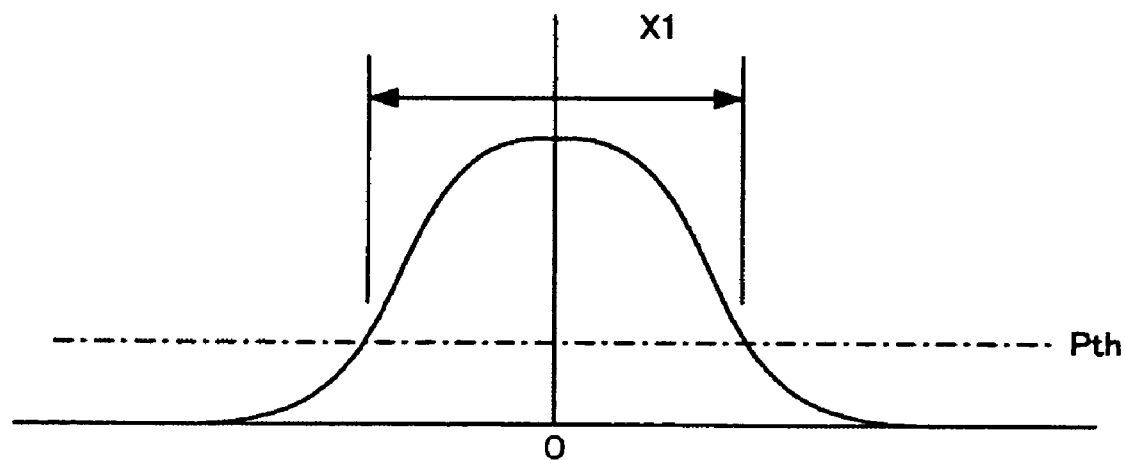
WHEN REFLECTANCE OF SAMPLE IS HIGH
F I G. 7 A
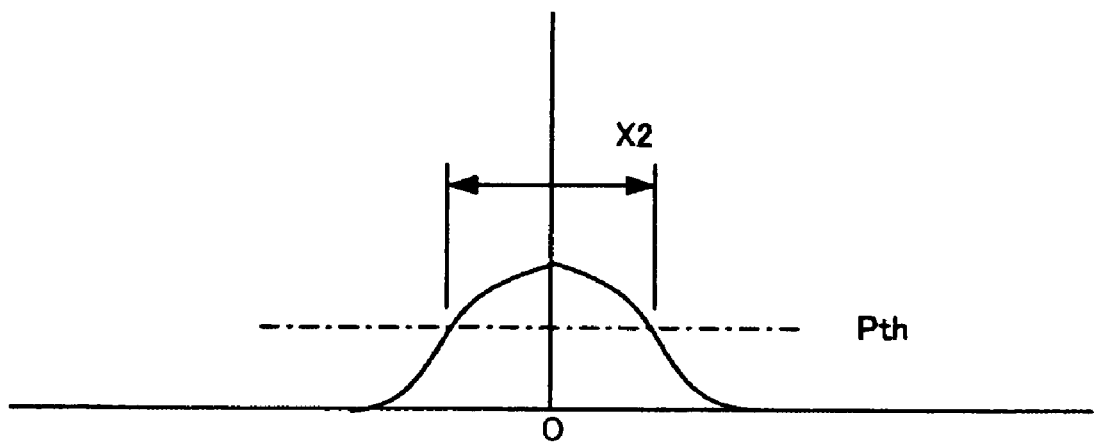
WHEN REFLECTANCE OF SAMPLE IS LOW
F I G. 7 B

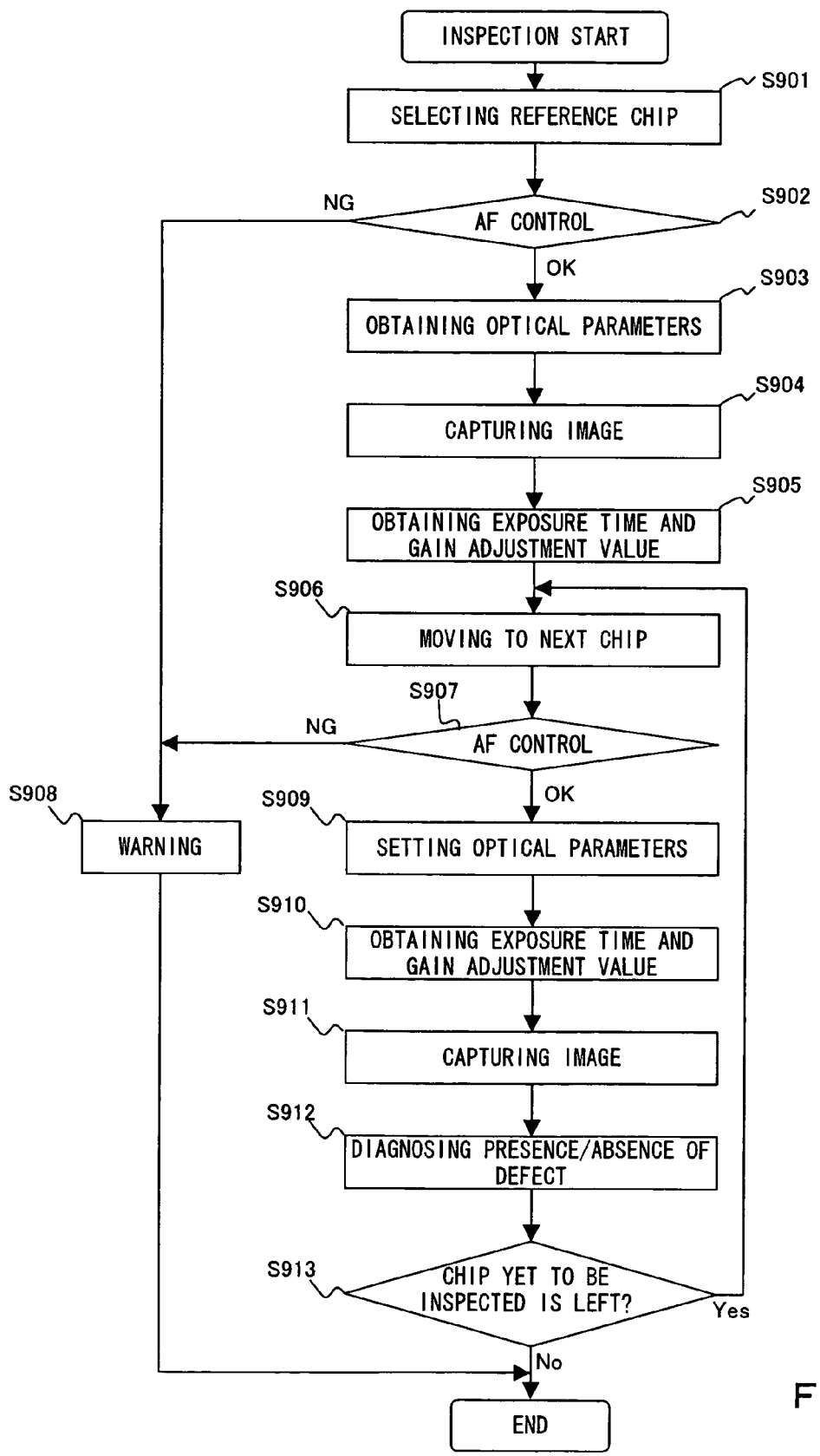
F I G. 9

DEFECT INSPECTION APPARATUS AND DEFECT INSPECTION METHOD

BACKGROUND OF THE INVENTION

1. Field of the Invention

The present invention relates to a defect inspection apparatus of a chip comparison inspection method, which automatically detects a defect of a semiconductor wafer, and a defect inspection method.

2. Description of the Related Art

In recent years, wiring rules have been becoming minute with the innovation of semiconductor technology, and the demand for detecting a defective chip with high accuracy at high speed has been growing in a semiconductor wafer inspection apparatus.

Accompanying this, the automation of a semiconductor wafer inspection apparatus using a microscope has been advancing, and an AF (automatic focusing) function for automatically achieving focus on an observation object has become an essential function. The performance of the AF function included in such an apparatus plays a very important role in improvements in, so-called, an inspection throughput (inspection efficiency per unit time).

For example, an semiconductor wafer automatic defect inspection apparatus of a chip comparison inspection method makes a matching (pattern matching) between a pattern of a normal chip verified beforehand and that of a chip to be inspected by taking advantage of the fact that a number of identical pattern chips are aligned and formed on a semiconductor wafer. If the apparatus determines that the patterns mismatch, it judges that an abnormal condition occurs in the chip to be inspected, and analyzes the contents of the abnormal condition.

With this automatic defect inspection apparatus, the AF is executed respectively when the pattern image of the normal chip is recognized, and when the pattern image of the chip to be inspected is captured. Therefore, the apparatus requires an AF operation time by the amount of time of the AF. Additionally, if focusing accuracy is poor, and if the image of the normal chip or the chip to be inspected becomes, so-called, defocused, the apparatus can erroneously judge the normal chip as an abnormal chip when making the pattern matching.

In the meantime, as a technology for improving AF performance such as a focusing speed and focusing accuracy, for example, Japanese Patent Publication No. H06-165019 discloses an automatic focusing apparatus switching a calculation method of a defocusing amount used to determine the focusing of AF control according to the luminance of a sample. Furthermore, Japanese Patent Application Laid-open No. H11-84228 discloses an automatic focus adjustment apparatus switching an algorithm of AF control according to brightness, which is an observation condition.

SUMMARY OF THE INVENTION

A defect inspection apparatus according to one preferred embodiment of the present invention comprises: a pattern image obtaining unit obtaining the pattern image of a predetermined part by causing an observation part of an observation object to be changed to the predetermined part within the observation object, and by causing focusing control to be performed in order to achieve focus on the predetermined part according to set focusing control parameters; a pattern image storing unit storing the pattern image obtained by the pattern image obtaining unit; and a detecting unit detecting the presence/absence of an abnormal condition of the part to be inspected and the contents of the abnormal condition (defect) by making a comparison between the pattern image, which is stored in the pattern image storing unit and obtained by the pattern image obtaining unit, of a reference part determined to be normal beforehand within the observation object, and the pattern image, which is obtained by the pattern image obtaining unit, of a part to be inspected, which becomes a target of inspecting the presence/absence of a defect within the observation object. The focusing control parameters, which are used for the focusing control performed when the pattern image obtaining unit obtains the pattern image of the part to be inspected, are determined based on sample information obtained by the focusing control performed when the pattern image obtaining unit obtains the pattern image of the reference part.

BRIEF DESCRIPTION OF THE DRAWINGS

FIG. 4 is a flowchart exemplifying the defect inspection process of a semiconductor wafer chip, according to the first preferred embodiment;

FIG. 5 is a flowchart exemplifying an AF control process executed in S403 or S409;

FIG. 6 exemplifies AF parameters used for AF control performed for a chip to be inspected;

FIG. 7A exemplifies the characteristic of the Z position of a stage, and the sum signal of the two-partitioning detector for a sample having a different reflectance;

FIG. 7B exemplifies the characteristic of the Z position of the stage, and the sum signal of the two-partitioning detector for a sample having a different reflectance;

FIG. 9 is a flowchart exemplifying the defect inspection process of a semiconductor wafer chip, according to a third preferred embodiment.

DESCRIPTION OF THE PREFERRED EMBODIMENTS

Hereinafter, preferred embodiments according to the present invention are explained with reference to the drawings.

Figure 1:
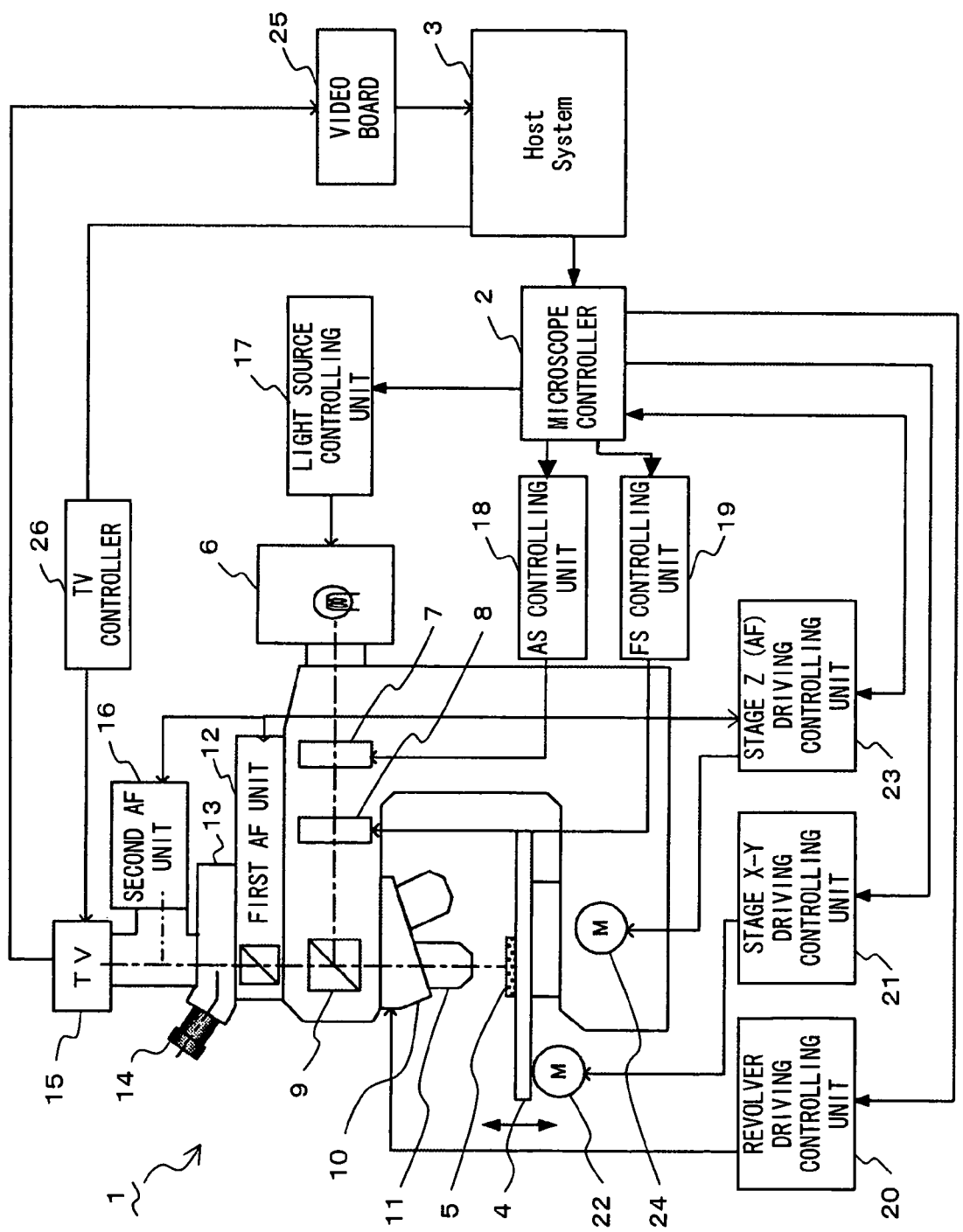
FIG. 1 exemplifies the configuration of a microscope system according to a first preferred embodiment of the present invention.

FIG. 1 exemplifies the configuration of a microscope system according to a first preferred embodiment of the present invention. The microscope system shown in this figure is one example of the configuration of an semiconductor wafer automatic defect inspection apparatus of a chip comparison inspection method.

As shown in this figure, this system comprises a microscope 1, a microscope controller 2, a host system 3, etc.

The microscope 1 comprises a light source 6 for incident-light illuminating a sample 5, which is an observation object placed on a stage movable in the upward and downward, and right and left directions (XYZ directions). Illumination light from the light source 6 is incident to the sample 5 via an aperture stop (AS) 7, a field stop (FS) 8, a cube 9 changing an observation method, and an objective lens 11 attached to a revolver 10. A pencil of light from the sample 5 passes through the objective lens 11 and a first AF unit (AF sensor head) 12, and its portion is guided to an eyepiece lens 14 by a tube 13. The other pencils of light are incident to a TV camera 15 and a second AF unit (AF sensor head) 16.

The host system 3 controls the operations of the whole of the system. For example, the host system 3 controls the microscope 1, etc. via the microscope controller 2.

The microscope controller 2 performs actual driving control for each electric control part via a respectively corresponding controlling unit under the control of the host system 3.

For example, illumination light intensity control of the light source 6 is performed according to a light source control instruction from the microscope controller 2, and a light source controlling unit 17 supplies power according to the control instruction to the light source 6. Additionally, the control of the aperture stop 7 and that of the field stop 8 are performed according to control instructions from the microscope controller 2 in a similar manner. An aperture stop (AS) controlling unit 18 drives the aperture stop 7 according to the control instruction, and a field stop (FS) controlling unit 19 drives the field stop 8 according to the control instruction. Furthermore, the driving control of the revolver 10 is performed according to a control instruction from the microscope controller 2 in a similar manner, and a revolver driving controlling unit 20 drives the revolver 10 according to the control instruction. As a result, the revolver 10 is rotated, and the magnification, etc. of the objective lens 11 on an optical path are changed. The move control of the stage 4 is performed according to control instructions from the microscope controller 2 in a similar manner. A stage X-Y driving controlling unit 21 drives a motor 22 according to the control instruction to move the stage 4 in the XY direction, whereas a stage Z driving controlling unit 23 drives a motor 24 according to the control instruction to move the stage 4 in the Z direction.

Furthermore, an AF control function is embedded in the stage Z driving controlling unit 23, which moves the stage 4 upward and downward based on the defocus amount for the sample 5, which is detected by the first and the second AF units 12 and 16 and will be described later, to guide the sample 5 to a focusing position.

In the meantime, the image of the sample 5, which is captured by the TV camera 15, is obtained by the host system 3 with a video board 25, and the host system 3 can store the obtained image in an image memory not shown. Additionally, the host system 3 can make the ON/OFF setting of automatic gain control and a gain setting, and the ON/OFF setting of automatic exposure control and an exposure time setting for exposure in the TV camera 15 via the TV controller 26.

Figure 2:
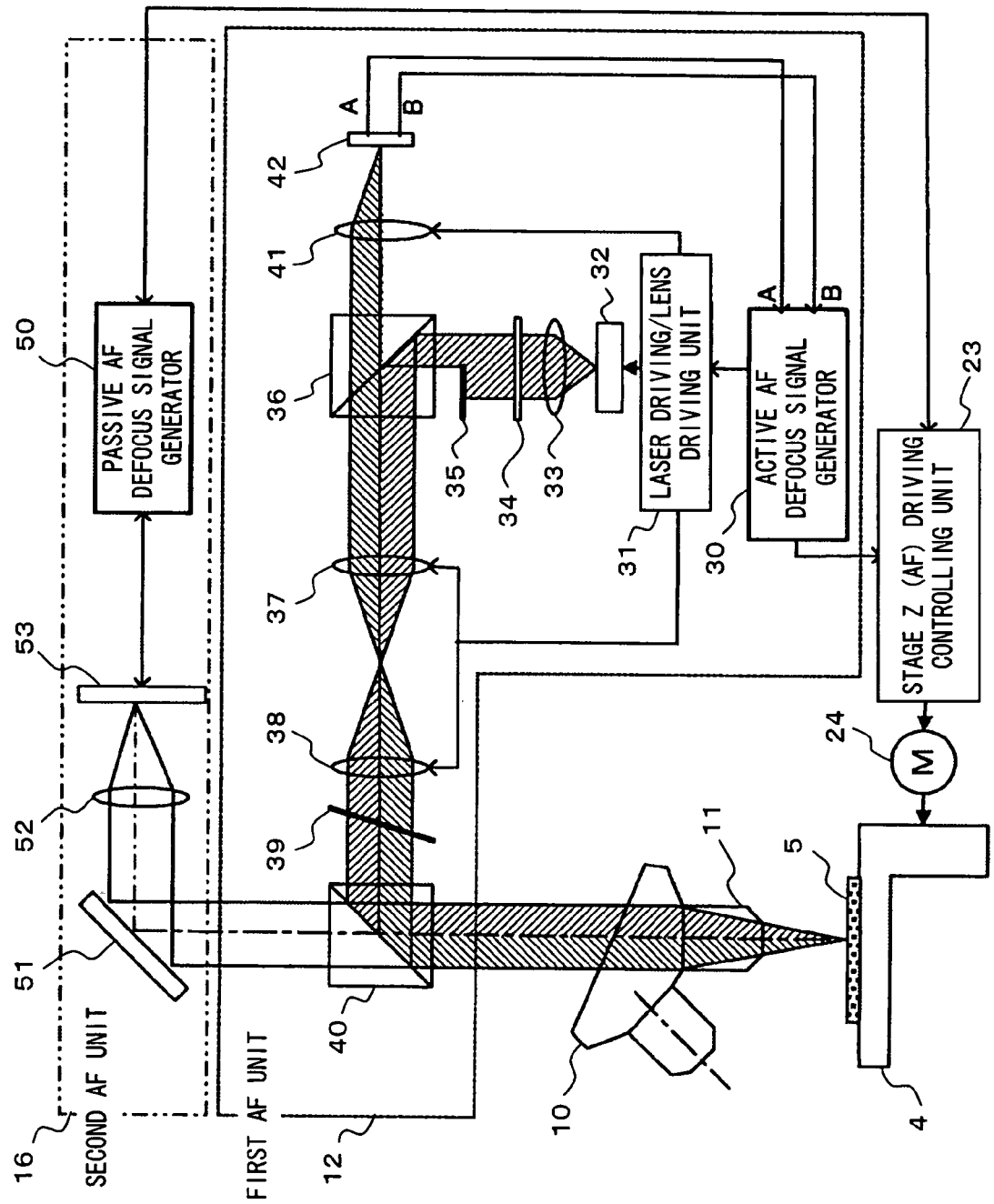
FIG. 2 shows the details of the configurations of a first AF unit and a second AF unit.

FIG. 2 shows the details of the configurations of the above described first AF unit 12 and second AF unit 16.

In this figure, the first AF unit 12 adopts an active AF method of a pupil partitioning type, which is one of active AF methods illuminating infrared laser light, etc. on a sample and performing AF control by using the light reflected from the sample. In the meantime, the second AF unit 16 adopts a passive AF method of a mountain climbing type, which is one of passive AF methods performing AF control by using the light image of a sample formed on an image capturing element such as a CCD, etc. Namely, this system adopts a hybrid AF method including the active and the passive AF methods.

Normally, for the characteristics of the AF performance implemented by both of the methods, the active AF method has an advantage in a focusing speed over the passive AF method, which depends on a focal depth, whereas the passive AF method, which actually achieves focus on the light image of a sample, has an advantage in focusing accuracy over the active AF method, which detects a distance to a sample.

However, with the passive AF method, the presence/absence of a contrast cannot be detected if a semiconductor wafer, which becomes a sample, is a mirror surface, etc. Therefore, in this system inspecting a defect of a semiconductor wafer, precedence is given to the active AF method in consideration of the throughput and an adaptive sample.

In the first AF unit 12 shown in FIG. 2, a laser light source 32 emits p-polarized laser light when a laser driving signal from a laser driving/lens driving unit 21 is input. The p-polarized laser light is converted into parallel pencils of light by a collimate lens 33, and passes through a visible cut filter 34 so that visible light included in the laser light is not irradiated on the sample 5. The pencils of light that pass through the visible cut filter 34 are incident to a polarized light beam splitter 36 via a shield 35 for shielding a half of the parallel pencils of light. The polarized beam splitter 36 has a characteristic such that a p-polarized light component is reflected, and an s-polarized light component passes through in order to reflect the pencils of light, which are not shielded by the shield 35, by 90°. The laser light reflected by the polarized light beam splitter 36 passes through a ¼ wavelength plate 39 via an image forming system lens group 37 and 38, is put into elliptically polarized light, and incident to the sample 5 via the objective lens 11 with a dichroic mirror 40 that is installed on the optical axis of the objective lens 11 and reflects only the wavelength of the laser light. In this figure, a path on which such laser light from the laser light source 32 is incident to the sample 5 is represented by being hatched to the right.

The laser light reflected from the sample 5 returns on the incident optical path, is put into an s-polarized light component, which passes through the polarized light beam splitter 36, by the ¼ wavelength plate 39, image-formed by an image forming lens 41, and incident to a two-partitioning detector 42 of an integral photoreceptor, as shown by being hatched to the left in this figure. Outputs according to the incident position (outputs on sides A and B) are input to an AF defocus signal generator 30 (also referred to simply as a signal generator 30 hereinafter). Then, the signal generator 30 generates a corresponding defocus signal based on the output of the two-partitioning detector 42, and outputs the generated signal to a stage Z driving controlling unit 23.

The image forming system lenses 37, 38, and 41 are configured to be movable according to a lens driving signal from the laser driving/lens driving unit 31. By moving any of the lenses, the wavelength of the irradiated laser light and a wavelength to be observed can be, so-called, parfocused (for example, a focus position according to the wavelength of irradiated laser light is matched with a focus position according to the wavelength to be observed, or the like), or an offset can be provided to the focus position.

Figure 3A:
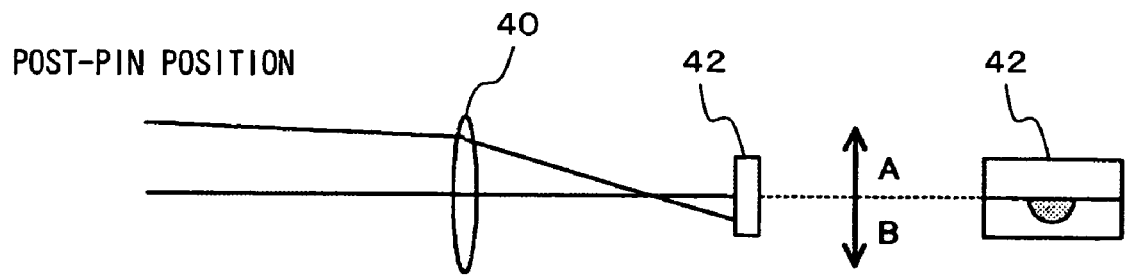
FIG. 3A shows the defocus characteristic of a two-partitioning detector.
Figure 3B:
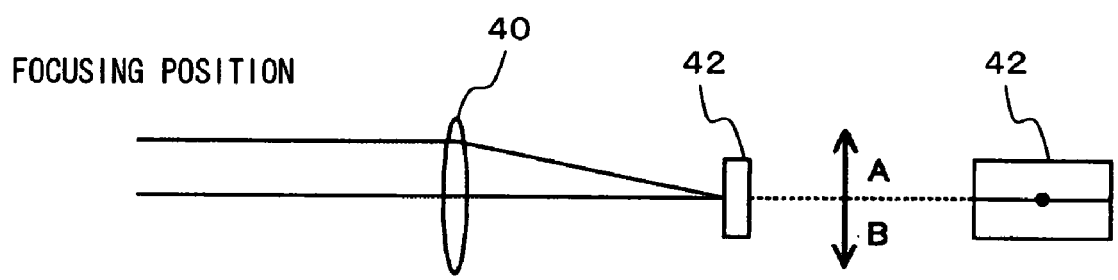
FIG. 3B shows the defocus characteristic of the two-partitioning detector.
Figure 3C:
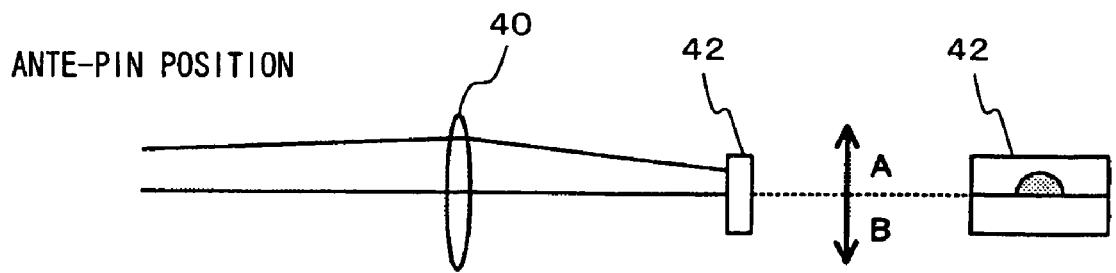
FIG. 3C shows the defocus characteristic of the two-partitioning detector.

FIGS. 3A, 3B, and 3C show the defocus characteristic of the two-partitioning detector 42 of the first AF unit 12 thus configured.

As shown in FIG. 3A, if the sample 5 is, so-called, in a post-pin position in which the sample 5 is under the focus position, the light reflected from the sample 5 is incident to the side B of the two-partitioning detector 42, which is a photoreceptor.

Additionally, as shown in FIG. 3B, if the sample 5 is in the focus position, the light, which has the same amount and is reflected from the sample 5, is incident to the sides A and B of the two-partitioning detector 42.

Furthermore, as shown in FIG. 3C, if the sample 5 is, so-called, in an ante-pin position in which the sample is above the focus position, contrary to the position shown in FIG. 3A, the light reflected from the sample 5 is incident to the side A of the two-partitioning detector 42.

With such a defocus characteristic, the active AF in the first AF unit 12 shown in FIG. 2 is executed as follows.

The active AF defocus signal generator 30 generates a defocus signal which represents the amount of defocus of the sample 5 based on the outputs of the sides A and B of the two-partitioning detector 42, and outputs the defocus signal to the stage Z driving controlling unit 23. The stage Z driving controlling unit 23 drives the motor 24 based on the defocus signal to move the stage 4 in the Z direction so that the defocus amount becomes 0, namely, the outputs of the sides A and B become equal. As a result, the sample 5 is guided to the focusing position. Additionally, the signal generator 30 outputs the sum signal of the outputs of the sides A and B of the two-partitioning detector 42 to the stage Z driving controlling unit 23 as occasion demands. Then, the stage Z driving controlling unit 23 can determine whether or not the sample 5 is close to the focusing position.

In the meantime, in the second AF unit 16 shown in FIG. 2, the light image of the sample is returned by a half mirror 51, and formed on a CCD sensor 53 by an image forming lens 52. The output of the CCD sensor 53 is input to a passive AF defocus signal generator 50 (also referred to simply as a signal generator 50 hereinafter). Then, the signal generator 50 generates a corresponding defocus signal based on the output of the CCD sensor 53, and outputs the generated signal to the stage Z driving controlling unit 23.

The passive AF in the second AF unit 16 having such a configuration is executed as follows.

The passive AF defocus signal generator 50 performs a known contrast operation such as the integral value of a difference between adjacent pixels based on an image signal (the output of the CCD sensor 53) captured by the CCD sensor 53, and outputs the result of the contrast operation to the stage Z driving controlling unit 23 as a defocus signal. The stage Z driving controlling unit 23 drives the motor 24 based on the defocus signal (the result of the contrast operation) to move the stage 4 in the Z direction so that the contrast of the image projected on the CCD sensor 53 becomes a maximum. As a result, the sample 5 is guided to the focusing position.

Additionally, the defocus signal generated by the signal generator 30 with the active AF, and the defocus signal (the result of the contrast operation) generated by the signal generator 50 with the passive AF are, as described above, input to the stage Z driving controlling unit 23, which can use each AF method depending on a use purpose, or can detect the defocus state implemented with the passive AF while executing the active AF.

Additionally, the stage Z driving controlling unit 23 includes a memory (not shown) for storing data, and can store various types of data (AF parameters, etc.) about the AF control, which are output from the host system 3.

A defect inspection process of a semiconductor wafer chip is explained next as one of control processes executed by the host system 3 of the microscope system configured as described above.

FIG. 4 is a flowchart exemplifying the defect inspection process.

In this figure, a semiconductor wafer, which becomes a sample, is placed on the stage 4. Once the defect inspection process is started, the stage 4 is first moved to a preset reference chip position in step S401. The reference chip is a chip that is verified to be normal beforehand.

In S402, default values are set as AF parameters used for the AF control for the reference chip. Note that the default values are values considered to allow the AF control to be performed for every sample. Examples of the AF parameters include a stage speed when the AF control is performed, a stage Z range (search range), a passive AF contrast threshold value (a first predetermined value), etc., which will be described later.

In step S403, the AF control for the reference chip is started according to the AF parameters set in the preceding step, and focus is achieved. The AF control performed in this step will be described later with reference to FIG. 5.

In step S404, AF parameters (AF parameters for feedback) used for the AF control for a chip to be inspected, which is performed next, are obtained based on sample information obtained by the AF control performed in the preceding step. The sample information is information, for example, about the focusing position of the reference chip, the amount of light according to the light reflected from the reference chip, and the like. Additionally, the AF parameters to be obtained are parameters optimum for obtaining a fast focusing speed, and high focusing accuracy in the AF control performed for the chip to be inspected. Examples of these AF parameters include a stage speed and a stage Z range (search range), etc. optimum for obtaining a high focusing speed, a passive AF contrast threshold value (a first predetermined value) optimum for obtaining high focusing accuracy, and the like. Such AF parameters obtained in this step will be described later with reference to FIG. 6.

In S405, the image of the reference chip, the focus of which is achieved in S403, is obtained via the video board 25.

In S406, the image of the reference chip, which is obtained in the preceding step, is stored in the memory of the host system 3.

When the image of the reference chip is thus obtained, the obtainment of the image of the chip to be inspected is started.

Firstly, in S407, the stage 4 is moved to the position of the chip to be inspected.

In S408, the AF parameters obtained in the above described S404 (the AF parameters for feedback) are set as the AF parameters used for the AF control for the chip to be inspected.

In S409, the AF control for the chip to be inspected is started according to the AF parameters set in the preceding step, and focus is achieved. The AF control performed in this step will be described later with reference to FIG. 5.

In S410, the image of the chip to be inspected, the focus of which is achieved in the preceding step, is obtained via the video board 25.

In S411, a matching between the pattern of the image of the reference chip, which is stored in the above described S406, and that of the image of the chip to be inspected, which is obtained in the preceding step, is made. If the patterns mismatch, the chip to be inspected is determined to be an abnormal chip. If the patterns match, the chip to be inspected is determined to be a normal chip. Namely, the presence/absence of a defect, and the contents of the defect are diagnosed in this step. The contents of the defect are, for example, a disconnection of a wiring pattern, the adhesion of dust, etc.

In S412, it is determined whether or not a chip to be inspected, which is yet to be inspected, is left. If the result of the determination is "Yes", the flow goes back to S401. If the result of the determination is "No", this flow is terminated. With such a determination, the above described process is repeatedly executed until a chip to be inspected, which is yet to be inspected, is not left.

The flow shown in FIG. 4 is executed, so that the AF parameters optimum for improving the focusing speed and the focusing accuracy in the AF control for a chip to be inspected are set based on sample information obtained by the AF control for the reference chip. Accordingly, high-speed and highly accurate AF control can be performed for a chip to be inspected, and high defect detection accuracy and a high throughput can be implemented in the defect inspection of a semiconductor wafer.

In this flow, the image of the reference chip and that of the chip to be inspected are obtained alternately. However, images of a plurality of chips to be inspected may be obtained for the image of a single reference chip, and a pattern matching with the image of each of the chips to be inspected may be made by using the image of the single reference chip.

FIG. 5 is a flowchart exemplifying the AF control process executed in the above described S403 or S409.

In this figure, once the AF control is started, the stage 4 is first moved to the lower limit position, which is set as one of the AF parameters, of the stage Z range (search range) for which the AF control is performed in S501.

In S502, the move of the stage 4 is started in the direction of the upper limit position of the above described stage Z range at a stage speed SP1 set as one of the AF parameters.

In S503, it is determined whether or not the stage 4 reaches the upper limit position of the above described stage Z range. If the result of the determination is "Yes", the flow goes to S510. If the result of the determination is "No", the flow goes to S504.

In S504, it is determined whether or not a contrast value according to the defocus signal (a result of a contrast operation) output from the passive AF defocus signal generator 50 is equal to or larger than the first value predetermined as one of the AF parameters. If the result of the determination is "Yes", the flow goes to S505. If the result of the determination is "No", the flow goes to S506.

In step S505, the position (stage address) of the stage 4 at this time is stored as Z1.

In S506, it is determined whether or not the sum signal of the outputs of the sides A and B of the two-partitioning detector 42, which is output from the active AF defocus signal generator 30, is equal to or larger than the second value predetermined as one of the AF parameters. If the result of the determination is "Yes", the stage 4 is determined to be close to the focusing position, and the flow goes to S507. If the result of the determination is "No", the stage 4 is determined to be far from the focusing position, and the flow goes back to S503.

As described above, with this system, the determination of whether or not the stage 4 is close to the focusing position is made with the result of the detection made by the first AF unit 12 by giving precedence to the active AF method. This is because if a semiconductor wafer, which becomes a sample, is a mirror surface, etc., the presence/absence of a contrast cannot be detected with the passive AF method, and a proper determination cannot possibly be made.

In S507, focusing is achieved by the first AF unit 12 with the active AF method. Namely, the position of the stage 4 is controlled so that the outputs of the sides A and B of the two-partitioning detector 42 become equal, and the focusing is achieved by the first AF unit 12 with the active AF method.

In S508, the defocus signal (the result of the contrast operation) output from the passive AF defocus signal generator 50 is obtained in the position of the stage 4 when the focusing is achieved in the preceding step, and it is determined whether or not the contrast value according to the defocus signal is equal to or larger than the above described first predetermined value. If the result of the determination is "Yes", the flow goes to S509. If the result of the determination is "No", the flow is terminated.

In S509, the stage 4 is moved so that the contrast value according to the defocus signal output from the passive AF defocus signal generator 50 becomes a maximum. Namely, the focusing is achieved by the second AF unit 16 with the passive AF method, and this flow is terminated.

In the meantime, the above described processes in S503 to S506 are repeated, and the sum signal of the outputs of the sides A and B of the two-partitioning detector 42 does not become equal to or larger than the second predetermined value in the whole of the stage Z range (search range), for which the AF control is performed, namely, if the result of the determination in the above described S503 is "Yes", it is determined in the succeeding S510 whether or not there is a position of the stage 4, in which the contrast value according to the defocus signal output from the passive AF defocus signal generator 50 is equal to or larger than the first predetermined value in the processes in S503 to S506 executed in the whole of the stage Z range, namely, whether or not there is the position of the stage 4, which is stored as Z1 in the above described S505. If the result of the determination is "Yes", the flow goes to S511. If the result of the determination is "No", the flow goes to S512.

In S511, the stage 4 is moved to the position stored as Z1, and the flow goes to the above described S509, in which the focusing is achieved with the passive AF method.

In S512, the move of the stage 4 is started in the direction of the lower limit position of the above described stage Z range at a stage speed SP2 set as one of the AF parameters. However, this stage speed SP2 is set as a speed lower than the stage speed SP1 in order to increase the possibility of achieving the focus.

In S513, it is determined whether or not the stage 4 reaches the lower limit position. If the result of the determination is "Yes", this flow is terminated. If the result of the determination is "No", the flow goes to S514.

In S514, it is determined whether or not the contrast value according to the defocus signal (the result of the contrast operation) output from the passive AF defocus signal generator 50 is equal to or larger than the above described first predetermined value. If the result of the determination is "Yes", the flow goes to S509, in which the focusing is achieved with the passive AF method. If the result of the determination is "No", the flow goes back to S513. In this way, this determination is repeated until the contrast value is determined to be equal to or larger than the first predetermined value up to when the stage 4 reaches the lower limit position of the stage Z range.

As described above, the flow shown in FIG. 5 is executed, whereby the AF control is performed according to the default values set in the above described S402, or the AF parameters for feedback, which are set in S408, as the AF parameters. Additionally, when the AF control is performed according to the AF parameters for feedback, high-speed and highly accurate AF control can be implemented. This is because the parameters are optimum values for obtaining a fast focusing speed and high focusing accuracy.

The control for detecting whether or not the sum signal of the outputs of the sides A and B of the two-partitioning detector 42 is equal to or larger than the second predetermined value while moving the stage 4 is called sample capturing control using the active AF method, whereas the control for detecting whether or not the contrast value according to the defocus signal output from the passive AF defocus signal generator 50 is equal to or larger than the first predetermined while moving the stage 4 is called sample capturing control using the passive AF method.

The AF parameters, which are obtained based on the sample information acquired with the AF control performed for the above described reference chip and used for the AF control performed for the chip to be inspected, are described next.

FIG. 6 exemplifies the AF parameters.

In this figure, an active AF stage speed indicates the fastest stage speed at which a sample search can be made when the sample search is made with the active AF method, namely, the fastest stage speed at which sample capturing can be made when the sample capturing control using the active AF method is performed, and is an AF parameter that contributes to an improvement in the focusing speed. This is obtained based on the amount of light (sample information) reflected from the sample, which is obtained when the AF control is performed for the reference chip. In the explanation of FIG. 5, this active AF stage speed is defined as the stage speed SP1 when the AF control for the chip to be inspected is performed. This stage speed will be described in detail later with reference to FIGS. 7A and 7B.

Additionally, a search range indicates the minimum stage Z range (the range of the stage 4 in the Z direction), for which the sample capturing can be made when the AF control is performed, and is an AF parameter that contributes to an improvement in the focusing speed. This is obtained based on the focusing position (sample information) obtained when the AF control is performed for the reference chip, and a range in the vicinity of the focusing position of the reference chip is defined as the search range for the chip to be inspected when the AF control is performed.

For example, if the focusing position of the sample is completely unknown, the AF control must be performed by setting an extensive search range. With this system, however, the focusing position of the chip to be inspected can be identified to some extent by detecting the focusing position with the AF control for the reference chip. Therefore, with the AF control for the chip to be inspected, the stage Z range when the AF control for the chip to be inspected is performed can be set to a narrow range by using a vicinity of the focusing position of the reference chip as the search range, whereby the focusing speed can be improved by reducing the search time. In the explanation of FIG. 5, this search range is defined as the stage Z range when the AF control is performed for the chip to be inspected.

Additionally, a sample search AF method indicates any of the active AF method, the passive AF method, and the hybrid AF method as an AF method when a sample is searched, and is an AF parameter that contributes to an improvement in the focusing speed.

For example, if the sum signal of the outputs of the sides A and B of the two-partitioning detector 42 is not determined to be equal to or larger the second predetermined value as a result of performing the AF control for the reference chip in the flows shown in FIGS. 4 and 5 ("No" in S506), the possibility that the sum signal of the outputs of the chip to be inspected is determined to be equal to or larger than the second predetermined value is also considered to be low. Accordingly, the sample search AF method when the AF control for the chip to be inspected is performed is limited to the passive AF method based on the sample information obtained when such AF control for the reference chip is performed, whereby the sample search using the active AF in method can be made not to be performed when the AF control is performed for the chip to be inspected is performed, and a meaningless process can be prevented from being executed. As a result, the focusing speed can be improved.

Additionally, a passive AF stage speed indicates the fastest stage speed at which the sample search can be made when the sample search using the passive AF method is made, namely, the fastest stage speed at which sample capturing can be made when the sample capturing control using the passive AF method is performed, and is an AF parameter that contributes to an improvement in the focusing speed. This is obtained based on the amount of light (sample information) reflected from the sample, which is obtained when the AF control for the reference chip is performed. In the explanation of FIG. 5, the passive AF stage speed is defined as the stage speed SP2 when the AF control for the chip to be inspected is performed. However, as described above, the stage speed SP2 is defined as a speed lower than the stage speed SP1 in order to increase the possibility of achieving focusing. The stage speed will be described in detail later with reference to FIGS. 7A and 7B.

Additionally, an active AF offset amount indicates the offset amount at the focusing position when the AF control using the active AF method is performed, and is an AF parameter that contributes to an improvement in the focusing accuracy. The active AF offset amount is not obtained by the AF control for the reference chip, but set, for example, by a person who makes a measurement.

For example, when focusing is achieved with the active AF method for the chip to be inspected if a film is coated on either the reference chip or the chip to be inspected, high focusing accuracy can be secured by offsetting the thickness of the film from the focusing position based on the active AF offset amount.

Additionally, a passive AF contrast threshold value indicates a threshold value optimum for detecting the presence/absence of a contrast, and contributes to an improvement in the focusing accuracy. This is obtained based on the amount of light (sample information) reflected from the sample, which is obtained when the AF control for the reference chip is performed. In the explanation of FIG. 5, the passive AF contrast threshold value is defined as the first predetermined value.

Here, the above described stage speed when the AF control is performed for the chip to be inspected is performed is further explained in detail in order to deepen understanding.

FIGS. 7A and 7B exemplify the characteristic of the Z position of the stage 4 and the sum signal of the two-partitioning detector 42 for samples having different reflectances. FIG. 7A shows the characteristic of a sample having high reflectance, whereas FIG. 7B shows the characteristic of a sample having low reflectance. In FIGS. 7A and 7B, the horizontal axis indicates a Z coordinate (the Z position of the Z stage 4), and the vertical axis indicates the sum signal of the two-partitioning detector 42. Additionally, the position in which the Z coordinate is 0 indicates the focusing position, and indicates a position in which the light reflected from the sample is the highest.

As shown in FIGS. 7A and 7B, a difference between the reflectances of the samples is a difference between ranges where the light reflected from the samples can be detected in the Z direction of the stage 4. Assuming that the level of the sum signal, at which a sample is determined to be close to the focusing position from the S/N, etc. of the signal, is Pth, the capturing range of the sample having the high reflectance, which is shown in FIG. 7A, is X1, and the capturing range of the sample having the low reflectance, which is shown in FIG. 7B, is X2, and the ranges have proportionalities with the reflectances. For the sample having the high reflectance, the sample capturing can be performed in a position more apart from the focusing position than the sample having the low reflectance.

In the sample capturing control, the stage speed when a sample is captured has a close relationship with this sample capturing range. The wider the sample capturing range, the higher the stage speed can be improved. As a result, a fast focusing speed can be obtained. Accordingly, the stage speed must be set to the lowest by assuming the case where the reflectance of an unknown sample is the lowest within the specifications by which the AF control can be performed for the sample, when the AF control is made for an unknown sample. If the reflectance of a sample is detected when the AF control for the reference chip is performed as in this system, and if it is known, a suitable stage speed can be set according to the detected reflectance of the sample when the AF control is performed for the chip to be inspected, so that the focusing speed can be improved.

As described above, according to this preferred embodiment, in the semiconductor wafer automatic defect inspection apparatus of a chip comparison inspection method, fast and highly accurate AF control can be performed for a chip to be inspected by feeding back the sample information obtained by the AF control for the reference chip when the AF control is performed for the chip to be inspected, whereby the inspection accuracy and the throughput can be dramatically improved.

To this preferred embodiment, the hybrid AF method that respectively adopts the pupil partitioning type and the mountain climbing type as the active AF method and the passive AF method is applied. However, it is not necessary that the AF method is the hybrid method in the control process for feeding back the sample information obtained when the AF control for the reference chip is performed, when the AF control for the chip to be inspected is performed. A similar effect can be obtained also by replacing the AF method referred to in this preferred embodiment with a known AF method.

Additionally, this preferred embodiment is configured so that the sample is guided to the focusing by moving the stage 4 on which the sample is placed in the Z direction (upward and downward directions). However, a similar effect can be obtained also with a configuration such that the sample is guided to the focusing position by moving the objective lens 11 in the Z direction.

Furthermore, this preferred embodiment is configured so that the observation part of the sample is changed by moving the stage 4 on which the sample is placed in the XY direction (right and left directions) However, a similar effect can be obtained also with a configuration such that the observation part of the sample is changed by moving the objective lens 11 in the XY direction.

A second preferred embodiment according to the present invention is explained next.

The configuration of a microscope system according to this preferred embodiment is similar to that shown in FIGS. 1 and 2. However, a defect inspection process of a semiconductor wafer chip, which is one of control processes, is different from that shown in FIG. 4. Here, the defect inspection process is explained.

Figure 8:
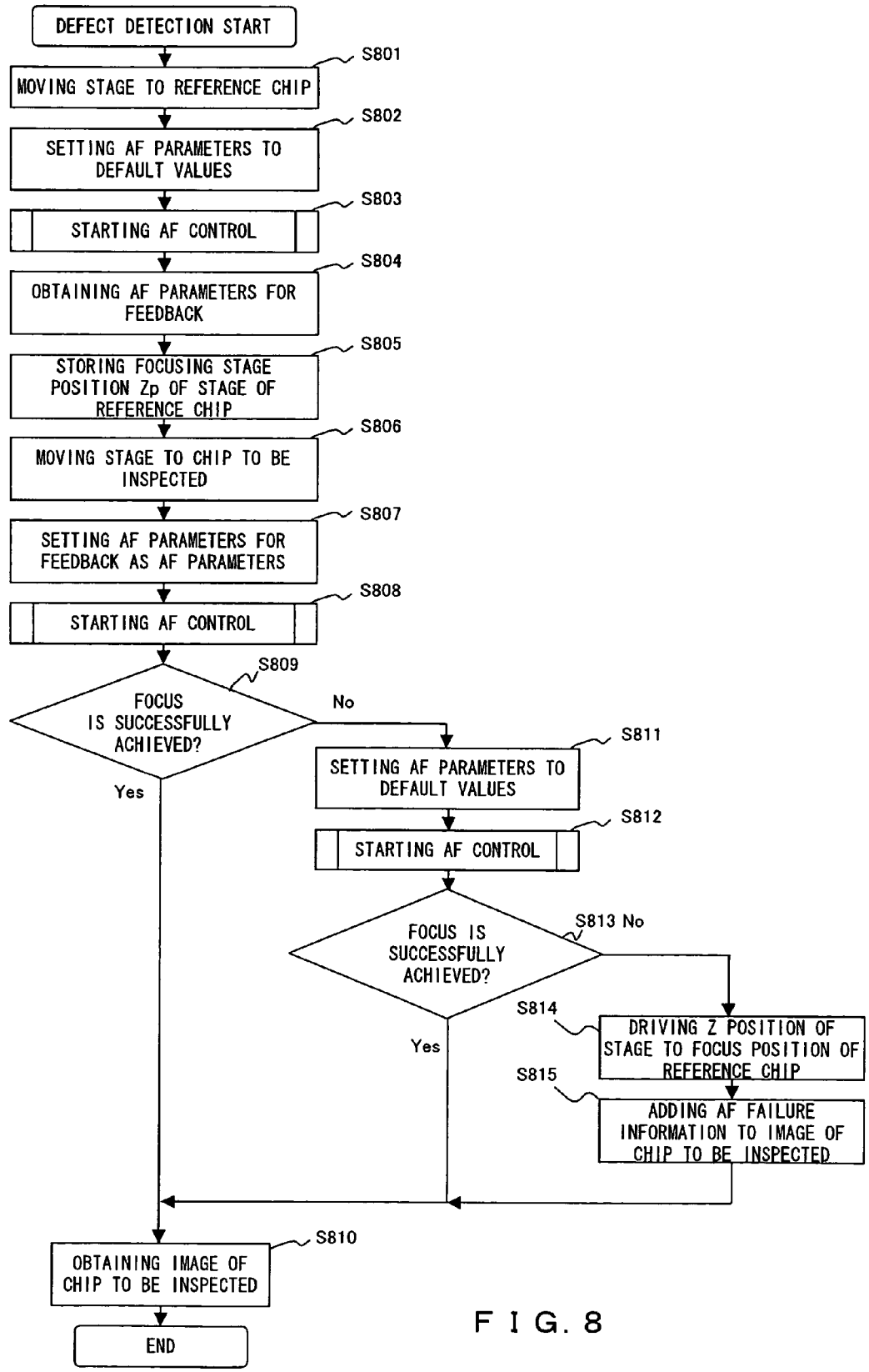
FIG. 8 is a flowchart exemplifying the defect inspection process of a semiconductor wafer chip, according to a second preferred embodiment.

FIG. 8 is a flowchart exemplifying the defect inspection process of a semiconductor wafer chip, according to the second preferred embodiment.

In this figure, in S801 to S804, processes similar to those in the above described S401 to S404 are executed.

In S805, a position in which focusing is achieved in S803, namely, the focusing position Zp of the reference chip is stored. Additionally, the image of the reference chip, for which focusing is achieved at this time, is obtained via the video board 25, and stored in the memory of the host system 3.

In S806, the stage 4 is moved to the position of the chip to be inspected.

In S807, AF parameters (AF parameters for feedback), which are obtained in S804, are set as AF parameters for the AF control performed for the chip to be inspected.

In S808, the AF control for the chip to be inspected is started according to the AF parameters set in the preceding step, and focusing is achieved. The AF control in this step is performed according to the above described flow shown in FIG. 5 (the same control is performed in S812).

In S809, it is determined whether or not the focus is properly achieved in the preceding step, namely, whether or not the focus is successfully achieved for the chip to be inspected. If the result of the determination is "Yes", the flow goes to S810. If the result of the determination is "No", the flow goes to S811.

In S810, the image of the chip to be inspected at this time is obtained via the video board 25. A matching between the pattern of the image of the reference chip, which is stored in the above described S805, and that of the image of the chip to be inspected, which is obtained in this step, is made. If the patterns mismatch, the chip to be inspected is determined to be an abnormal chip. If the patterns match, the chip to be inspected is determined to be a normal chip. Namely, the presence/absence of a defect, and the contents of the defect are diagnosed.

In the meantime, if the AF control for the chip to be inspected is unsuccessfully performed, namely, if the result of the determination made in S809 is "No", the set AF parameters are initiated to default values in the succeeding S811. Namely, the AF parameters for feedback set as the AF parameters are destroyed and reset to the default values, whereby the AF parameters are changed from the AF parameters for feedback to the default values.

In S812, the AF control is restarted according to the default settings made in the preceding step, and focus is achieved.

In S813, it is determined whether or not the focus is properly achieved in the preceding step, namely, whether or not the focusing is successfully achieved for the chip to be inspected. If the result of the determination is "Yes", the flow goes to the above described S810. If the result of the determination is "No", the flow goes to S814.

In S814, the stage 4 is moved to the stage position Z stored in the above described S805. This step is a process executed to obtain the image of the chip to be inspected by regarding the focusing position of the reference chip as the focusing position of the chip to be inspected, because the focusing is unsuccessfully achieved in both of the AF control according to the AF parameters for feedback and that according to the default values.

In S815, information about the unsuccessful focusing achievement (unsuccessful AF control) for the chip to be inspected is added to the image of the chip to be inspected, which is to be obtained in S810, and the flow goes to S810. As a result, the information about the unsuccessful focusing achievement is added to the obtained image of the chip to be inspected in the succeeding step S810. Thereafter, it can be notified that the defect detection accuracy of the image can be possibly low.

As described above, according to this preferred embodiment, in the semiconductor wafer automatic defect inspection apparatus of the chip comparison inspection type, even when a chip abnormal condition, which makes the AF control difficult, such as the occurrence of a through hole, the existence of a large foreign substance, etc. in the chip to be inspected occurs, the defect detection can be securely made. As a result, the detection accuracy and the throughput can be dramatically improved.

A third preferred embodiment according to the present invention is explained next.

The configuration of a microscope system according to this preferred embodiment is similar to that shown in FIGS. 1 and 2. However, a defect inspection process of a semiconductor wafer chip, which is one of control processes, is different from that shown in FIG. 4 or 8. Accordingly, that defect inspection process is explained here.

FIG. 9 is a flowchart exemplifying the defect inspection process of a semiconductor wafer chip, according to the third preferred embodiment.

In this figure, a semiconductor wafer, which becomes a sample, is placed on the stage 4. Once the defect inspection process is started, a reference chip verified to be normal is first selected in S901, and the stage 4 is moved to the position of the reference chip.

In S902, default values are set as AF parameters used for the AF control performed for the reference chip, and the AF control is performed according to the default values. It is then determined whether or not focusing is successfully achieved (whether or not a focusing operation is properly completed). If the result of the determination is "Yes"("OK" in this figure), the flow goes to S903. If the result of the determination is "No" ("NG" in this figure), the flow goes to S908. The default values are as described above in the explanation of the first preferred embodiment. Additionally, the AF control in this step is performed according to the flow shown in FIG. 5.

In S903, the aperture diameter of an aperture stop 7, and a voltage set in the light source controlling unit 17, which are optical parameters for controlling the amount of illumination light irradiated on the semiconductor wafer, are obtained and stored. The amount of the illumination light emitted from the light source 6 is controlled according to the voltage set in the light source controlling unit 17.

Additionally, in this step, AF parameters (AF parameters for feedback) used for the AF control performed for the chip to be inspected are obtained based on sample information obtained by the AF control performed in the preceding step. The AF parameters are as described above in the explanation of the first preferred embodiment.

In S904, for the TV camera 15, the ON setting of automatic gain control is made, and at the same time, the ON setting of automatic exposure control is made. Then, image capturing is performed for the reference chip, so that the image of the reference chip is obtained.

In S905, a gain adjustment value and exposure time when the image capturing is performed in the preceding step are obtained and stored.

In S906, the stage 4 is moved to the position of the next chip, namely, the position of the chip to be inspected.

In S907, the AF control for the chip to be inspected is performed according to the AF parameters obtained in the above described S903, and it is determined whether or not the focusing is successfully achieved (whether or not the focusing operation is properly completed). If the result of the determination is "Yes" ("OK" in this figure), the process goes to S909. If the result of the determination is "No" ("NG" in this figure), the flow goes to S908. The AF control in this step is performed according to the flow shown in FIG. 5.

In S908, a warning display is made since the focusing is unsuccessfully achieved. As a result, the process is aborted, and the flow is terminated.

In S909, the aperture diameter and the voltage, which are the optical parameters stored in the above described S903, are set in the aperture stop 7 and the light source controlling unit 17.

In S910, the gain adjustment value and the exposure time, which are stored in the above described S905, are set in the TV camera 15.

In S911, image capturing is performed for the chip to be inspected, and the image of the chip to be inspected is obtained.

In S912, a matching between the pattern of the image of the reference chip, which is obtained in S904, and that of the image of the chip to be inspected, which is obtained in the preceding step, is made, and the presence/absence of a defect and the contents of the defect are diagnosed.

In S913, it is determined whether or not a chip to be inspected, which is yet to be inspected, is left. If the result of the determination is "Yes", the flow goes back to S906, in which the process for the next chip to be inspected is started. If the result of the determination is "No", this flow is terminated.

As described above, the flow shown in FIG. 9 is executed, so that the image capturing conditions of the reference chip and the chip to be inspected can be made to match. As a result, an ideal pattern matching can be made, and the defect detection can be made with higher accuracy.

As described above, according to this preferred embodiment, in the semiconductor wafer automatic defect inspection apparatus of a chip comparison inspection method, the image capturing conditions of a reference chip and a chip to be inspected can be further made to match, whereby the inspection accuracy and the throughput can be dramatically improved.

In the pattern matching process in this preferred embodiment, only a defective chip may be detected and output by giving precedence to the shortening of the inspection time. Additionally, the image of the defective chip may be stored with high resolution at that time. Furthermore, detailed image information can be securely saved, for example, if a memory, a RAM, etc. of a hard disk device, which is a large-capacity storage medium, or a portable storage medium such as a DVD-RAM, an MO, a CD-R, etc. is used as a storage medium in which the image is to be stored. Still further, if not a custom format but a normal image format such as JPEG, BMP, GIF, TIFF, etc. is applied as the format of an image stored onto these storage media, a defect position, a defect state, etc. can be analyzed with general image processing software. As a result, such an image processing function is omitted from this system, which can be configured cheaply.

A modification example of the microscope system according to this preferred embodiment is explained next.

Configuration of the microscope system according to this modification example is almost similar to that shown in FIGS. 1 and 2. However, a difference exists in a point that the light source controlling unit 20 newly comprises a photodetector for monitoring the output (illumination intensity) of the light source 6. Additionally, a defect inspection process of a semiconductor wafer chip, which is one of control processes of this system, is almost similar to that shown in FIG. 9. However, a difference exists in a point that the voltage obtained/stored in the above described S903 is not the voltage set in the light source controlling unit 17, but an opto-electrically converted value according to the output of the light source 6, which is obtained by the above described photodetector.

As described above, according to this modification example, the change amount of the output of the light source 6, which varies with time, can be corrected, whereby a more accurate amount of light can be given to the semiconductor wafer. Accordingly, the uniformity of more accurate image capturing conditions can be secured, and the defect detection with higher accuracy can be made.

As described above, the defect inspection apparatus and the defect inspection method according the present invention are explained in detail. However, the present invention is not limited to the above described preferred embodiments. Various types of improvements and modifications can be made in a scope which does not deviate from the gist of the present invention, as a matter of course.

As described above in detail, according to the present invention, in the semiconductor wafer automatic defect inspection apparatus of a chip comparison inspection method, the defect inspection accuracy and the throughput can be dramatically improved.

What is claimed is:

1. A defect inspection method, comprising:
  driving a stage or an objective lens facing an observation object in order to change an observation part of the observation object placed on the stage to a reference part determined to be normal beforehand within the observation object;
  performing focusing control with a focusing control unit which changes a relative distance between the stage and the objective lens in a direction of the optical axis of the objective lens so that automatic focusing is achieved on the reference part according to a first focusing control parameter;
  determining a second focusing control parameter based on sample information obtained when performing the focusing control to achieve the automatic focusing on the reference part using the first control parameter, wherein the sample information contains at least one of information about the focusing position of the reference part and information about a light amount according to light reflected from the reference part, and the second focusing control parameter contains at least one of movement speed used by said focusing control unit, search range used when acquiring the observation object, autofocus method, offset amount, and contrast threshold;
  performing focusing control so that focusing is achieved on the reference part according to the first focusing control parameter;
  obtaining a pattern image of the reference part;
  driving the stage or the objective lens in order to change the observation part of the observation object to a part to be inspected, which becomes a target of inspecting for the presence or absence of a defect within the observation object;
  performing the focusing control with the focusing control unit so that automatic focusing is achieved on the part to be inspected according to the second focusing control parameter; then
  obtaining a pattern image of the part to be inspected; and
  detecting the presence or absence of an abnormal condition of the part to be inspected by making a comparison between the pattern image of the reference part and the pattern image of the part to be inspected.

2. The defect inspection method according to claim 1, wherein:
  if the focusing control using the second focusing control parameter is unsuccessfully performed, the focusing control parameter is changed to the first focusing control parameter and the pattern image of the part to be inspected is obtained by performing the focusing control using the first focusing control parameter.

3. The defect inspection method according to claim 2, wherein:
  if the focusing control using the first focusing control parameter is unsuccessfully performed when obtaining the pattern image of the part to be inspected, the pattern image of the part to be inspected is obtained by regarding the focusing position of the reference part as the focusing position of the part to be inspected.

4. The defect inspection method according to claim 3, wherein:
  when the pattern image of the part to be inspected is obtained by regarding the focusing position of the reference part as the focusing position of the part to be inspected, information about unsuccessful focusing control is added to the pattern image of the part to be inspected.

5. The defect inspection method according to claim 1, wherein:
  after obtaining a reference image of the reference part, a plurality of inspection images of the reference part are obtained and defects are detected by comparing the plurality of inspected images with one reference image, respectively.

6. A defect inspection apparatus, comprising:
  a stage on which an observation object is placed;
  an objective lens for imaging the observation object;
  an observation part changing unit for changing an observation position of the observation object via the objective lens by moving at least one of the stage and the objective lens in a direction perpendicular to an optical axis of the objective lens;
  a focusing control unit for performing automatic focusing by changing a relative distance between the stage and the objective lens in a direction of the optical axis of the objective lens to focus on the observation object;
  a parameter setting unit for setting a focusing control parameter used for controlling the automatic focusing;
  a pattern image obtaining unit for obtaining a pattern image of an observation part by driving the observation part changing unit to change the observation position;
  a pattern image storing unit for storing the pattern image obtained by said pattern image obtaining unit;
  a detecting unit for detecting the presence or absence of a defect of a part to be inspected by making a comparison between the pattern image of a reference part in the observation object stored in the pattern image storing unit and the pattern image of the part to be inspected in the observation object;
  wherein said pattern image obtaining unit is arranged to obtain the pattern image of the reference part in the observation object determined as normal beforehand by performing the focusing control via the focusing control unit using a first focusing control parameter set by the parameter setting unit, and arranged to change the observation position to the part to be inspected and obtain the pattern image of the part to be inspected by performing the focusing control via the focusing control unit using a second focusing control parameter set by the parameter setting unit, and
  wherein said focusing control unit is arranged to determine the second focusing control parameter, used when obtaining the pattern image of the part to be inspected, based on sample information obtained when the pattern image of the reference part is obtained by performing the focusing control using the first focusing control parameter, wherein the sample information contains at least one of information about the focusing position of the reference part and information about a light amount according to light reflected from the reference part, and wherein the second focusing control parameter contains at least one of movement speed used by said focusing control unit, search range used when acquiring the observation object, autofocus method, offset amount, and contrast threshold.

7. The defect inspection apparatus according to claim 6, wherein if the focusing control using the second focusing control parameter is unsuccessfully performed when said pattern image obtaining unit obtains the pattern image of the part to be inspected, the focusing control parameter is changed to the first focusing control parameter and the pattern image of the part to be inspected is obtained by performing the focusing control using the first focusing control parameter.

8. The defect inspection apparatus according to claim 7, wherein if the focusing control using the first focusing control parameter is unsuccessfully performed when said pattern image obtaining unit obtains the pattern image of the part to be inspected, the pattern image of the part to be inspected is obtained by regarding the focusing position of the reference part as the focusing position of the part to be inspected.

9. The defect inspection apparatus according to claim 8, wherein when said pattern image obtaining unit obtains the pattern image of the part to be inspected by regarding the focusing position of the reference part as the focusing position of the part to be inspected, information about unsuccessful focusing control is added to the pattern image of the part to be inspected.

10. The defect inspection apparatus according to claim 6, wherein:

said pattern image obtaining unit obtains a plurality of inspection images of the reference part by operating said observation part changing unit after obtaining a reference image of the reference part and detects defects by comparing the plurality of inspected images with one reference image in the detection unit, respectively.

11. The defect inspection apparatus according to claim 6, wherein:

the reference part and the part to be inspected are provided in a specific position in the observation object having a plurality of same patterns and the patterns of the reference part and the inspection part are the same, respectively.

12. The defect inspection apparatus according to claim 11, wherein:

the presence or absence of a defect is detected by making a comparison between the pattern image of the reference part stored in said pattern image storing unit and the pattern image of the part to be inspected by said detecting unit, and if a different part is found in each pattern, the pattern image of the part to be inspected is determined to be abnormal and if the patterns are the same, they are determined to be normal.

13. The defect inspection apparatus according to claim 6, wherein:

the reference part and the part to be inspected are provided in a specific position in the observation object having a plurality of same patterns and the patterns of the reference part and the inspection part are the same, respectively.

14. The defect inspection apparatus according to claim 13, wherein:

the presence or absence of a defect is detected by making a comparison between the obtained pattern image of the reference part and the pattern image of the part to be inspected, and if a different part is found in each pattern, the pattern image of the part to be inspected is determined to be abnormal and if the pattern are the same they are determined to be normal.

* * * * *